United States Patent [19]

Blades

[11] Patent Number: 4,683,435

[45] Date of Patent: Jul. 28, 1987

[54] CIRCUIT FOR COMPENSATING NON-LINEARITIES IN ELECTROLYTE CONDUCTIVITY MEASUREMENT SYSTEM

[75] Inventor: Frederick K. Blades, Boulder, Colo.

[73] Assignee: Anatel Instrument Corporation, Boulder, Colo.

[21] Appl. No.: 689,871

[22] Filed: Jan. 9, 1985

[51] Int. Cl.$^4$ ............................................. G01N 27/06
[52] U.S. Cl. ...................................... 324/442; 204/406
[58] Field of Search ............... 324/442, 425, 441, 426, 324/430, 436, 439, 62, 428; 320/48; 204/406; 429/90; 307/359, 308; 328/162; 330/85, 290, 294, 1 A

[56] References Cited

U.S. PATENT DOCUMENTS 3,972,002  7/1976  Aprille, Jr. ........................ 330/294
4,227,151  10/1980  Ellis et al. ............................ 324/441

FOREIGN PATENT DOCUMENTS 0018375  2/1977  Japan ................................... 324/442
0129569  11/1978  Japan ................................... 330/85

Primary Examiner—Stewart J. Levy
Assistant Examiner—D. O'Shea
Attorney, Agent, or Firm—Saidman, Sterne, Kessler & Goldstein

[57] ABSTRACT

A circuit for measurement of the conductance of an electrolyte cell is disclosed which features compensation for non-linearities produced by resistance in series with the resistance of the cell and for non-linearities caused by polarization of the cell due to chemical, kinetic or other effects within the cell. The cell is driven by an AC signal, and the circuit features a feedback loop in which a portion of the AC output signal is fed back for compensation of the series resistance and in which an op-amp generates a compensating DC voltage, both of which are summed with the AC excitation signal prior to its being supplied to the cell.

4 Claims, 7 Drawing Figures

CIRCUIT FOR COMPENSATING NON-LINEARITIES IN ELECTROLYTE CONDUCTIVITY MEASUREMENT SYSTEM

FIELD OF THE INVENTION

The present invention relates to circuitry and instruments for the measurement of electrolyte conductivity. More particularly, a circuit is disclosed whereby non-linear effects introduced by either a constant resistance or a voltage source in series with the electrolyte resistance, or both, can be accurately compensated for.

BACKGROUND AND OBJECTS OF THE INVENTION

Electrolyte conductivity is a measure of a solution's ability to carry electric current. In an otherwise relatively nonconducting solution, the measure of electrolyte conductivity can provide a nonspecific though quantitative indication of the total level of ionized impurities present. Owing to the simplicity and relatively low cost of commercially available conductivity cells and meters, this technique has found widespread acceptance in many modern manufacturing processes. In the production of ultrapure water, for example, where large quantities of high purified water must be monitored to maintain the purity, conductivity measurements provide the principal measure of purity.

Specific conductance is defined as the conductance in mhos of one centimeter cube of the liquid at a specified temperature, commonly 25° C. Inversely, specific resistance is similarly defined as resistance in ohms of a one centimeter cube of the liquid at a specified temperature. The units of specific conductance and specific resistance are mhos/cm and ohm-cm respectively. Distilled water typically has a specific conductivity at room temperature of just less than one micromho/cm. Absolutely pure water has a conductivity of 0.055 micromho/cm. at 25° C.

Techniques for the measurement of electrolyte conductivity are well known in the prior art. Modern direct contact liquid conductivity sensing instruments generally comprise two electrodes positioned within the solution whose electrical resistance or conductance is to be measured. The electrodes are used to apply a constant voltage across a known volume of liquid, and the resultant current therethrough is measured. If a direct current voltage is applied across the cell electrodes, ion migration occurs, leading to inaccuracies due to the resultant changes in the composition of the solution adjacent to the electrodes. This effect is termed polarization. Therefore, alternating current is almost universally employed.

In addition to polarization effects induced by the measuring circuit, it has been found by the present inventor, and the literature shows, that polarization can occur due to both kinetic and chemical effects within the solution itself. If active chemical reactions are occurring in the sample solution, this effect can be quite pronounced. For example, see the copening application of Frederick K. Blades, et al, Ser No. 635,551, filed Aug. 2, 1984, incorporated by reference herein, in which an instrument is described having conductivity measuring electrodes exposed directly to short-wave ultraviolet radiation. It has been found that under these circumstances, the electrochemical activity at the surface of the electrodes, stimulated by the heavily oxidative environment caused by the presence of ultraviolet radiation, produces a net potential across the electrodes on the order of several hundred millivolts. Accurate compensation techniques must be employed if the solution conductivity in the presence of such an induced potential is to be accurately measured.

Accordingly, it is an object of the present invention to provide a circuit by which the effects of an induced, ordinarily slowly varying potential are accurately compensated for.

As mentioned, the instrument described in the copending application referred to above comprises a low pressure discharge ultraviolet light source situated in proximity to the conductivity measuring electrodes. The high voltage excitation required to operate such a lamp tends to induce noise in the measuring circuits, and it was found desirable to add a filter to attenuate the lamp noise in series with the conductivity measuring circuit. However, the effect of adding the filter is to introduce a constant resistance in series with the solution resistance being measured. A constant resistance in series with a varying solution resistance produces an undesirable non-linearity in the output signal.

Accordingly, it is a further object of the present invention to provide a circuit by which the non-linearity produced by a constant resistance in series with the cell resistance is accurately compensated for.

SUMMARY OF THE INVENTION

The present invention achieves the needs of the art and objects of the invention mentioned above by its provision of a circuit for the measurement of electrolyte conductivity whereby the effects of both a relatively constant DC potential and a constant resistance in series with the solution resistance can be accurately and economically compensated for. The circuitry comprises a feedback loop employing both AC and DC, positive and negative, feedback whereby a portion of the output signal is fed back to control the drive signal in a fashion directly but inversely proportional to the non-linear effects discussed, and thereby compensate for these effects.

BRIEF DESCRIPTION OF THE DRAWINGS

The invention will be better understood if reference is made to the accompanying drawings in which.

BRIEF DESCRIPTION OF THE PRIOR ART

Figure 1:
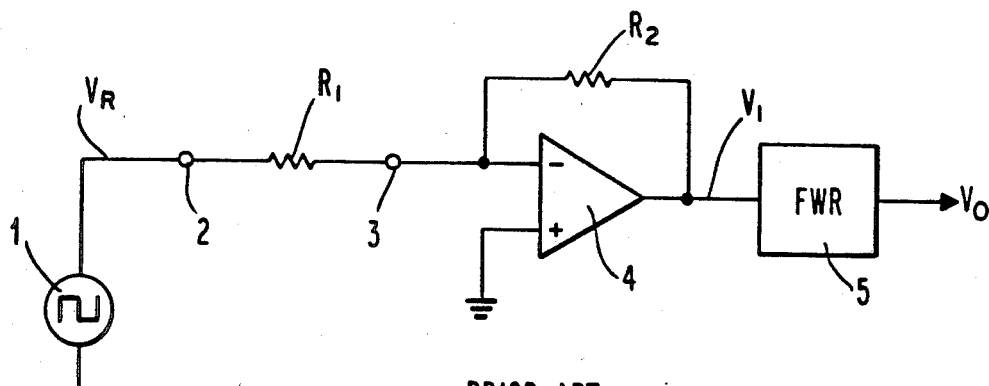
FIGS. 1 and 2 show prior art practices and illustrate how nonlinearities arise in circuits for measuring electrolyte conductivity.

To better illustrate the sources of non-linearity compensated for by the circuit of the present invention, a brief description is included of the general practices of the prior art. Referring now to FIG. 1, a signal source or oscillator 1 produces a constant amplitude AC signal $V_R$ which drives a first electrode 2 positioned within the solution the resistance $R_1$ of which is to be measured. The waveform is typically either a sine or square wave at a frequency ranging from 60–1000 Hz. A second electrode 3 receiving current in proportion to the conductance $\sigma_1 = 1/R_1$ of the solution feeds a standard current-to-voltage converter circuit, comprising an op amp 4 and a resistor R2. The output voltage $V_1$, is $$V_1 = \frac{-V_R R_2}{R_1} = -\sigma V_R R_2.$$

The output voltage $V_1$ is then fed through a conventional full-wave averaging rectifier (FWR) circuit 5 to produce a DC output voltage $V_0$, the level of which is proportional to the conductivity of the solution.

Figure 2:
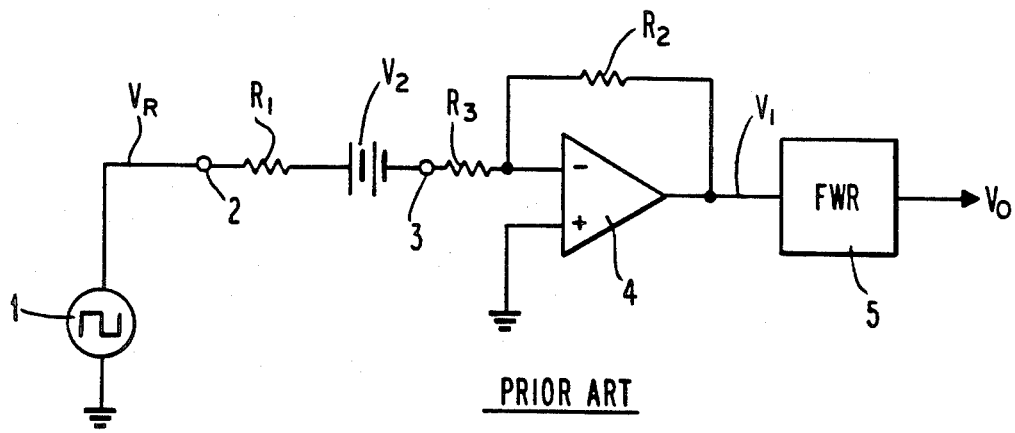

A similar circuit, with equivalents to typical sources of non-linearity, is shown in FIG. 2. The series battery $V_2$ represents the voltage produced within the measuring cell due to polarization at the measuring electrode solution interfaces. This signal is typically a slowly varying DC level and produces an output voltage dependent on its level:

$$V_1 = \frac{-(V_R + V_2)R_2}{R_1}.$$

Although it is readily apparent that this imposed DC voltage could be eliminated by the addition of a series capacitor, it will be apparent to those skilled in the art that this approach would produce a differentiator circuit having a frequency response dependent on the conductivity of the solution. Furthermore, since it is standard practice to utilize a square waveform to maintain precise amplitude control of the signal source, this effect can become quite pronounced.

In addition to the non-linearity thus produced, the addition of a series capacitor would adversely affect the high-voltage frequency noise rejection capability of the current-voltage converter, as this expedient would add a zero, and a resultant increase in gain with frequency.

Addition of a constant series resistance $R_3$ for filtering likewise produces an undesirable non-linearity in the output response:

$$V_1 = \frac{-V_R R_2}{R_1 + R_3}.$$

As can be seen, the output voltage $V_1$ decreases in a non-linear fashion with increasing solution conductance, asymptotically approaching a value proportional to the conductance of $R_3$.

The combined effect of these two non-linearities produces an output voltage $V_1$:

$$V_1 = \frac{-(V_R + V_2)R_2}{R_1 + R_3}.$$

BRIEF DESCRIPTION OF THE INVENTION

Although the circuit realized as the preferred embodiment of the present invention and described below in connection with FIG. 5 simultaneously compensates for both sources of non-linearity mentioned, the circuit techniques employed are more clearly described separately.

Figure 3:
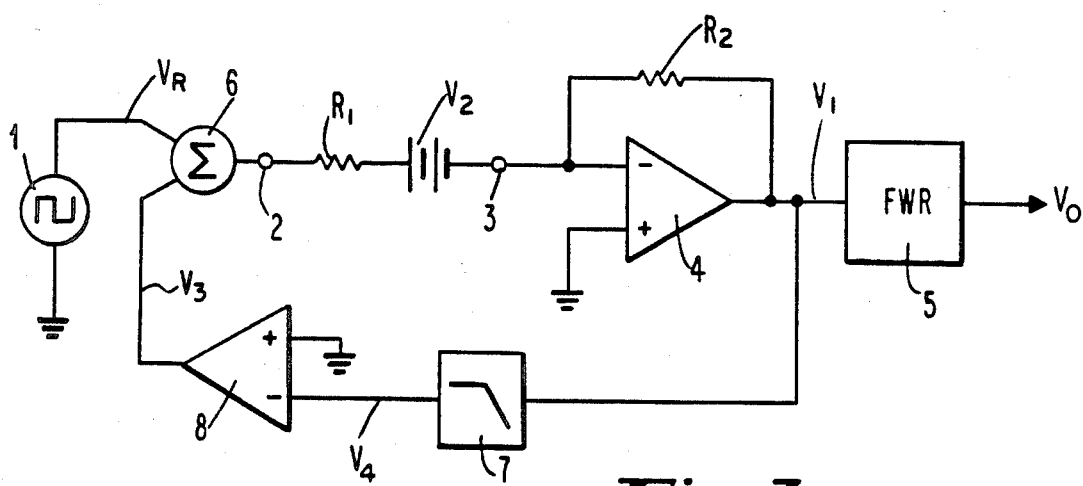
FIG. 3 shows a block diagram of a circuit which provides compensation for a relatively constant DC series voltage.

FIG. 3 shows a block diagram of a circuit which provides compensation for a relatively constant series DC voltage, as generated in certain conductance cells. Where not described, the circuit elements correspond to similarly numbered elements of the other figures. As shown, the DC component $V_4$ of the current-to-voltage converter 4 output $V_1$ is extracted via a low-pass filter 7 and compared to a (zero volts) ground reference in an op-amp 8. The output of op-amp 8 provides an error signal $V_3$ as follows:

$$V_3 = (0 - V_4)A$$

where
$V_4$ = DC component of $V_1$, and
$A$ = open loop gain of error amplifier 8, due to the fact that op-amps provide whatever output is necessary to drive their inputs to equality.

The error signal $V_3$ is summed with the signal source $V_R$ in summing junction 6, to provide a DC voltage at electrode 2 equal and opposite to the polarization-induced DC potential $V_2$. Thus, the solution resistance is effectively placed within a feedback loop and the error produced by $V_2$ is automatically compensated for by the open-loop gain of op-amp 8.

Figure 4:
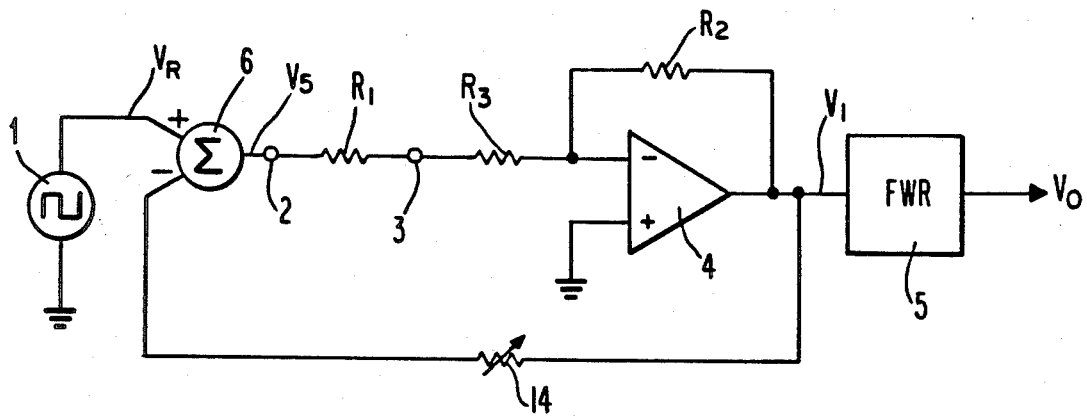
FIG. 4 shows a block diagram of a circuit for compensating non-linearity introduced by a constant series resistance.

Compensation for the non-linearity introduced by a constant series resistance $R_3$ (needed for filtering as discussed above) is illustrated in a similar feedback circuit shown in FIG. 4. In this case, a fraction K of the AC output signal $V_1$ (the fraction being determined by potentiometer 14) is fed back and summed with the signal source $V_R$ in summing junction 6, to precisely compensate for the reduction in current flowing through $R_1$ due to the presence of $R_3$. Now the drive signal $V_5$ is $V_R$ less a fraction K of $V_1$:

$$V_5 = V_R - KV_1 \tag{1}$$

If we now let $K = R_3/R_2$
Then $$V_5 = V_R - \frac{R_3 V_1}{R_2}$$

Then, since $$V_1 = \frac{-(V_5 R_2)}{R_1 + R_3}$$

Substituting:

$$V_1 = \frac{-(V_R R_2 - R_3 V_1)}{R_1 + R_3}$$

$$V_1(R_1 + R_3) = R_3 V_1 - R_2 V_R$$

$$V_1 R_1 + V_1 R_3 = V_1 R_3 - V_R R_2$$

$$V_1(R_1 + R_3 - R_3) = -V_R R_2$$

$$VY_1 = -V_R\left(\frac{R_2}{R_1}\right)$$

Thus, with K adjusted to equal $R_3/R_2$, the error introduced by $R_3$ is precisely compensated for. It will be recognized by those skilled in the art that this amounts to positive feedback and can be lead to unstable circuit response if not adequately compensated; as will be recognized by those skilled in the art, this need is addressed by the circuit of the invention, which will now be described.

DESCRIPTION OF THE PREFERRED EMBODIMENT

Figure 5:
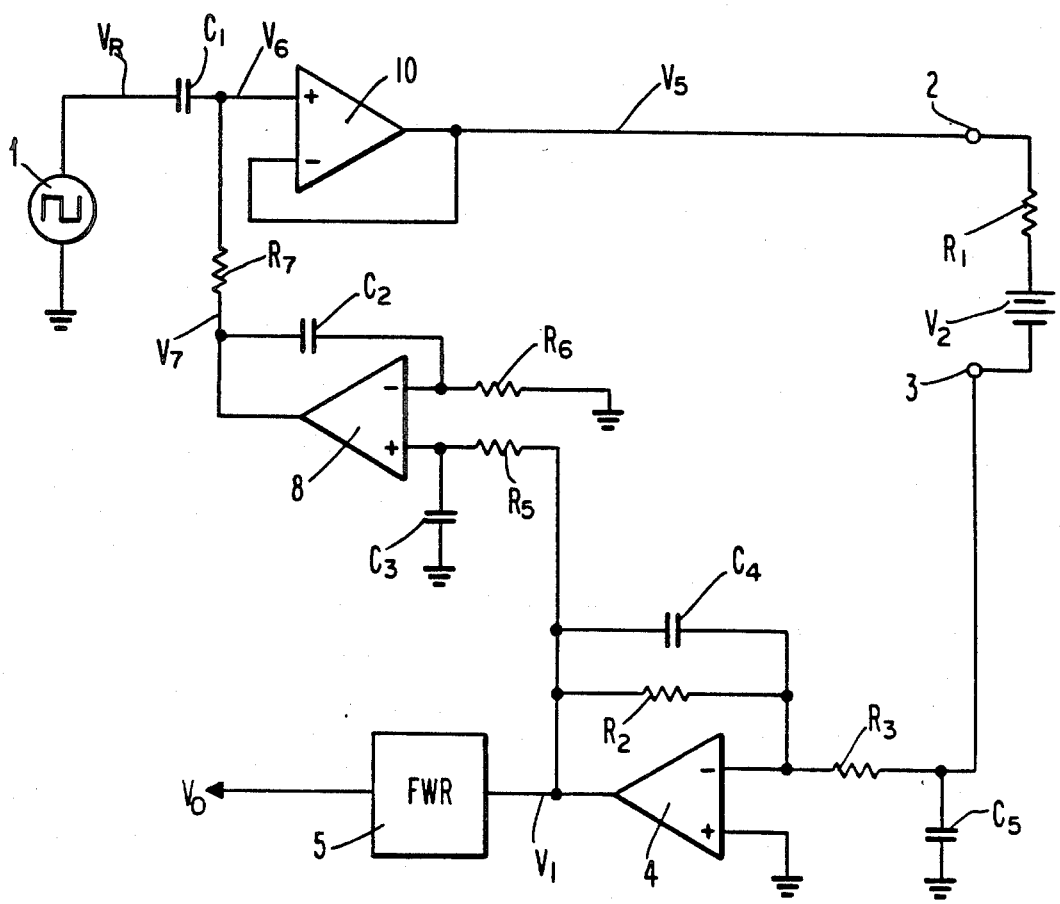
FIG. 5 shows a preferred embodiment of a circuit embodying the improvements of the circuits of FIGS. 3 and 4.

Referring now to FIG. 5, the preferred embodiment of the present invention is shown, a circuit which simultaneously incorporates the features of the two circuits described above. Where applicable, the reference numerals correspond to those of the other figures.

As shown, a constant amplitude square wave oscillator 1, serving as the source of signal $V_R$ for the conductivity measurement, is AC coupled through capacitor $C_1$ to the high impedance input of a buffer amplifier 10. Oscillators of this type are well known to those skilled in the art. In the present implementation, a frequency of 100 Hz was chosen and the rising and falling edges of the waveform slowed down to approximately 1/10 the period, to minimize cross-talk in the cell coupling wires and circuit leads.

Analyzing the DC loop performance first, it can be seen that a DC feedback loop is established whereby a single pole low-pass filter comprising $R_3$ and $C_5$ essentially extracts the DC component of $V_1$. This DC level is compared to ground, zero volts, in op-amp 8, operated as an integrator, producing a DC error voltage, which is amplified by the open loop gain of op-amp 8 and superimposed on the AC waveform present at the driving electrode 2. The loop is closed through the solution resistance $R_1$, and signal inversion is provided by input amplifier 4; a negative feedback loop is thus established.

Analyzing the DC equivalent circuit of FIG. 5:

$$V_1(dc) = \frac{(V_5(dc) - V_2)R_2}{R_1 + R_3}$$

Since $V_6$ will be driven to whatever value is required to force the inputs of error amplifier 8 equal:
$V_1(dc) = 0$ volts
Thus:
$V_5(dc) = V_2$ Consequently, a DC voltage equal and opposite to the induced series voltage $V_2$ is provided to the driving electrode 2, thereby forcing $V_1(dc)$ to zero volts and allowing essentially no direct current to flow through the measuring circuit due to the induced voltage $V_2$.

It will be appreciated that several simplifying assumptions have been made to better describe the circuit function. The first concerns the input bias currents and offset voltages of the operational amplifiers. These effects are readily understood and compensated for by selection of appropriate resistance values by one skilled in the art.

The second assumption is that the single pole low-pass filter comprising $R_5$ and $C_3$ accurately extracts the DC component of $V_1$. With reasonable values for $R_5$ and $C_3$, the AC signal level of $V_1$ is merely attenuated to perhaps 1 or 2% of the value present at $V_1$. This could cause appreciable non-linearities in the DC circuit, but instead, in fact, the AC feedback signal is utilized to compensate for the non-linearity introduced by series resistance $R_3$ needed for power supply-induced noise filtering.

To describe the AC feedback loop performance, one must first analyze the transfer functions of each block, then combine them to describe the full loop transfer function.

(Throughout this analysis, conventional Laplace-transform notation is used; in particular, $S = jw$).

Analyzing the current-to-voltage converter op-amp 4 first, the transfer function is (neglecting $V_2$):

$$\frac{V_1}{V_5} = -\left[\frac{\frac{R_2}{R_1 + R_3}}{(1 + R_2 C_4 S)\left(1 + \frac{R_1 R_2 C_5 S}{R_1 + R_3}\right)}\right]$$

If $R_1$ (minimum) $>> R_3$ then:

$$\frac{V_1}{V_5} \approx \frac{\frac{-R_2}{R_1 + R_3}}{(1 + R_2 C_4 S)(1 + R_3 C_5 S)}$$

Note that $R_3$ and $C_5$ serve to introduce an additional pole in the response to effect an overall two-pole low pass filter for noise attenuation.

Next, the transfer function of error amplifier 8 is examined:

$$\frac{V_7}{V_1} = \frac{R_6 C_2 S + 1}{R_6 C_2 S[R_5 C_3 S + 1]}$$

And finally, the summer, comprising $C_1$ and $R_7$, is analyzed:

$$V_6 = \frac{V_7}{R_7 C_1 S + 1} + \frac{V_R R_7 C_1 S}{R_7 C_1 S + 1}$$

The combined overall AC loop response produces:

$$V_5 = V_6 = \frac{[R_6 C_2 S + 1]V_1}{R_6 C_2 S[(R_5 C_3 S + 1)(R_7 C_1 S + 1)]} + \frac{V_R R_7 C_1 S}{R_7 C_1 S + 1} \quad (2)$$

It will be appreciated that the combined overall AC loop response of equation 2 given above is of the form of equation 1, i.e. $V_3 = V_R - KV_1$ $$\text{Thus } K = \frac{[R_6 C_2 S + 1]}{R_6 C_2 S[(R_5 C_3 S + 1)(R_7 C_1 S + 1)]}$$

As shown previously, in order to precisely compensate the non-linearity introduced by $R_3$ $$K = \frac{R_3}{R_2}$$

Thus, $$\frac{R_3}{R_2} = \frac{[R_6 C_2 S + 1]}{R_6 C_2 S[(R_5 C_3 S + 1)(R_7 C_1 S + 1)]}$$

Figure 6:
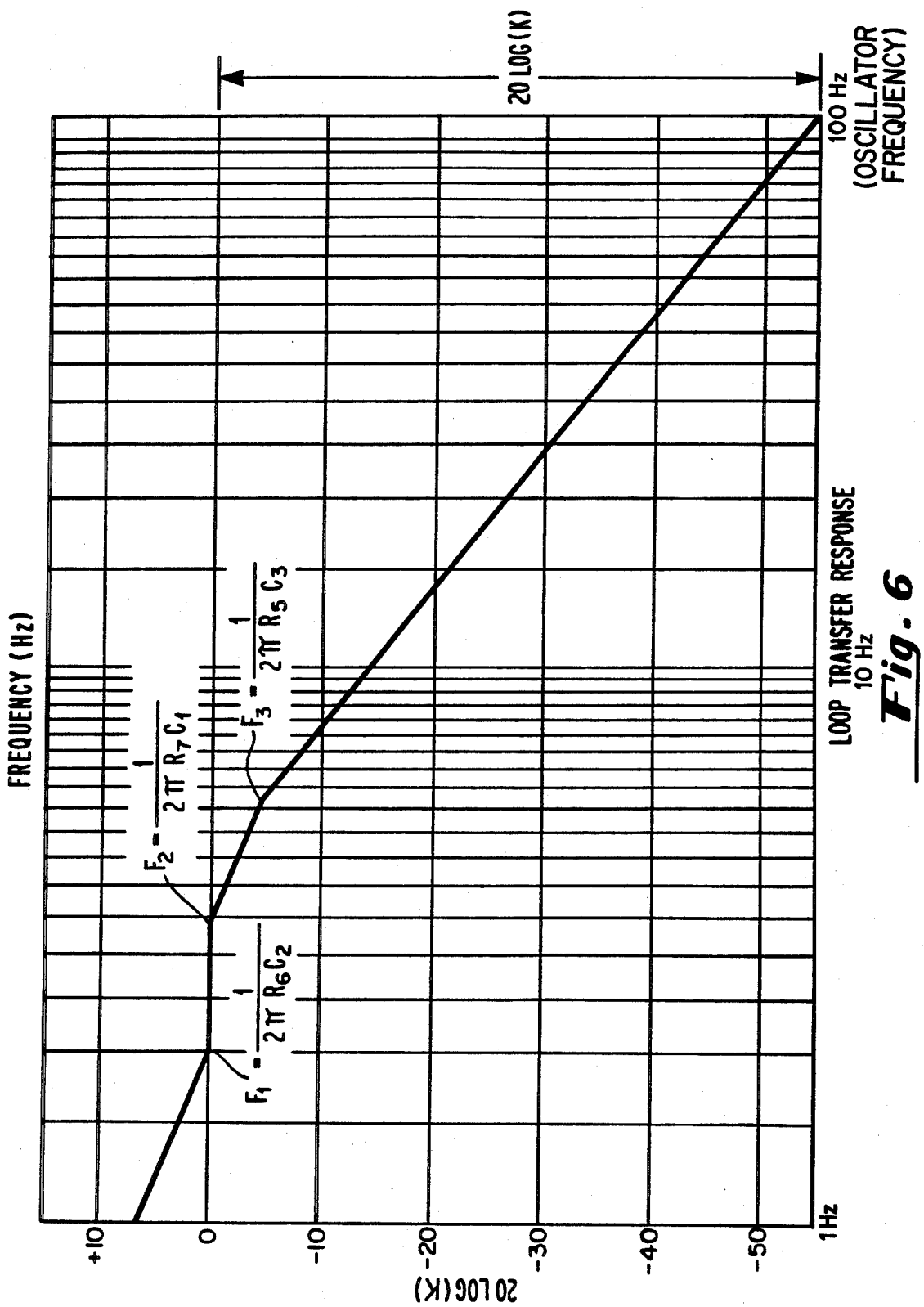
FIG. 6 shows a Bode plot of the loop transfer response of the circuit of FIG. 5.

Referring now to FIG. 6, the Bode plot of the magnitude of the loop attenuation factor K is shown, reflecting typical values for the components shown in FIG. 5; the several portions of the plot are marked with the relevant filter components.

Referring again to FIG. 6, it can be seen that the attenuation K produced at the oscillator frequency, 100 Hz in the example, must be made equal to $R_3/R_2$ to produce the desired compensation. The effect of this compensation is to vary the shape of the driving wave form with cell resistance in such a fashion as to precisely compensate for the non-linearity introduced by the equivalent series resistance $R_3$. As cell resistance decreases and the attenuating effect of $R_3$ becomes more pronounced, the flat top of the driving square wave form actually bows up to produce an effectively higher amplitude and thus compensate for this attenuation.

Figure 7:
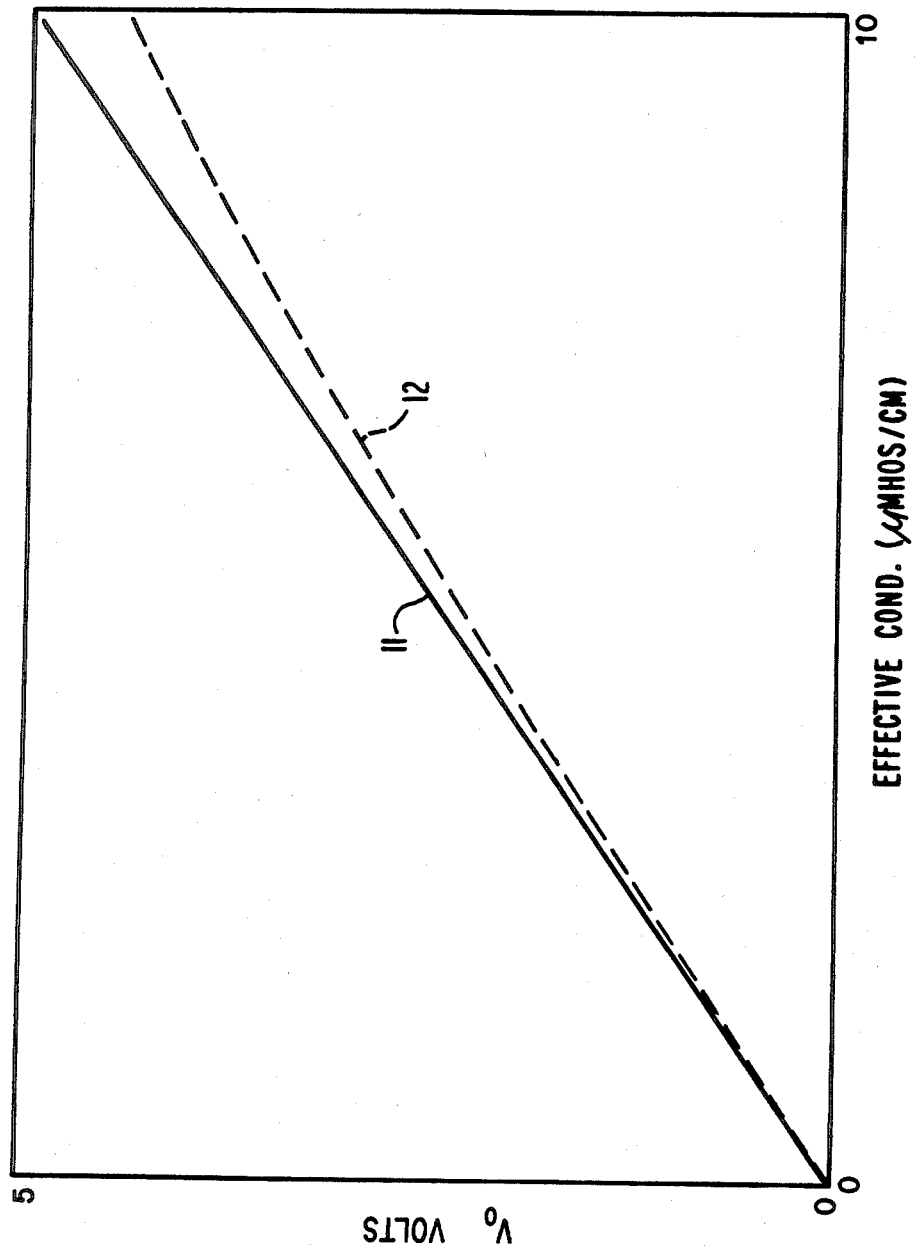
FIG. 7 shows a plot of the linearity of the circuit shown in FIG. 5.

FIG. 7 illustrates the conductivity response function of the circuit; plots 11 and 12 show the response, with and without the compensatory feedback loop, respectively. In this case, the maximum linearity error was reduced from 3.6% to less than .07% error.

While a preferred embodiment of the invention has been described, the invention should not be so limited, but only by the following claims.

I claim:

1. A circuit for measuring the resistance of an electrolyte cell comprising a pair of electrodes, said cell being juxtaposed to a source of high-frequency noise, comprising:

oscillator means, for supplying a relatively low-frequency AC excitation signal $V_R$, connected to one of said electrodes;

first filter means, connected to the other of said electrodes, for receiving and filtering a major component of said noise from an AC output signal from said cell, said filter introducing a nonlinearity into said AC output signal, current-to-voltage converter means connected to said filter means, for generating an output signal $V_1$, having an AC component proportional to the resistance of the cell and to the excitation signal $V_R$, and a DC component $V_2$;

a feedback loop comprising an integrator for generating a DC compensation signal equal to the DC component $V_2$ of $V_1$, said integrator introducing an AC nonlinearity into said output signal, wherein said first filter means and said integrator are chosen such that said AC nonlinearities are equal and opposite in sign; and means for summing said DC compensation signal with said AC input signal $V_R$.

2. The circuit of claim 1 further comprising full-wave rectifying means for generating a DC signal proportional to said output signal $V_1$.

3. Method for measuring the resistance of an electrolyte cell comprising a pair of electrodes, said cell being juxtaposed to a source of high-frequency noise, comprising the steps of:

applying a relatively low frequency AC excitation signal to one of said electrodes;

filtering an AC output signal received from the other of said electrodes to filter out a major component of said noise, said filtering introducing a nonlinearity in said AC output signal;

converting the filtered output signal to a voltage signal, said voltage signal including an AC component proportional to the resistance of the cell and a DC component from said cell;

integrating said output signal in a feedback loop, for generating a DC compensation signal equal and opposite to the DC component of the voltage signal, said DC compensation signal including a nonlinearity introduced in the integrating step, wherein said filtering and integrating steps are performed so that said nonlinearities are equal and opposite in sign; and summing the integrated output of said feed-back loop together with the excitation signal, thus compensating for said DC component.

4. The method of claim 3 further comprising the step of full-wave rectifying said voltage signal to generate a DC output signal proportional to the resistance of said cell.

* * * * *